(12) United States Patent
Pettit et al.

(10) Patent No.: US 6,943,194 B1
(45) Date of Patent: Sep. 13, 2005

(54) SYNTHESIS OF PHENSTATIN AND PRODRUGS THEREOF

(75) Inventors: George R. Pettit, Paradise Valley, AZ (US); Brian Toki, Linwood, WA (US)

(73) Assignee: Arizona Board of Regents, acting for and on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 09/582,952

(22) PCT Filed: Jan. 9, 1999

(86) PCT No.: PCT/US99/00475

§ 371 (c)(1),
(2), (4) Date: Jul. 7, 2000

(87) PCT Pub. No.: WO99/34788

PCT Pub. Date: Jul. 15, 1999

Related U.S. Application Data
(60) Provisional application No. 60/070,878, filed on Jan. 9, 1998.

(51) Int. Cl.$^7$ .............................................. A61K 31/185
(52) U.S. Cl. ...................... 514/576; 514/546; 514/679; 560/140; 562/24; 568/333
(58) Field of Search ................................. 514/576, 546, 514/649; 560/140; 562/24; 568/333, 648

(56) References Cited

U.S. PATENT DOCUMENTS 4,966,237 A * 10/1990 Swanson et al. ............ 514/646
5,430,062 A * 7/1995 Cushman et al. ........... 514/646

FOREIGN PATENT DOCUMENTS

JP 3-130216 6/1991

OTHER PUBLICATIONS

Diwadkar et al (Chem. Abstracts # 1962:462460; Current Science (1962), 31, 149–50; Ti –Lignans. II. Synthesis of benzophenones as intermediates for the synthesis of lignans, 1962) rn=22699–97–4.*

Gardner et al, Chem Abstract 1961:54194, rn=22699–97–4; 1961.*

Pettit, G. R. et al.; "Antineoplastic agents. 379. Synthesis of Phenstatin Phosphate.", Journal of Medicinal Chemistry, vol. 41, No. 10, pp. 1688–1695 (May 7, 1998).

Gschwend, Daniel A. et al., "Specificity in Structure–Based Drug Design: Identification of a Novel, Selective Inhibitor of *Pneumocystis carinii* Dihydrofolate Reductase," PROTEINS: Structure, Function, and Genetics, vol. 29, No. 1, pp. 59–67 (1997).

* cited by examiner

Primary Examiner—Samuel Barts
(74) Attorney, Agent, or Firm—Fennemore Craig, P.C.; Richard Mybeck

(57) ABSTRACT

A newly discovered antineoplastic compound denominated "phenstatin" is herein described as are synthetic methods for producing phenstatin and the active prodrug thereof. Phenstatin was converted to the sodium phosphate prodrug (3d) by a dibenzylphosphite phosphorylation and subsequent hydrogenolysis sequence 3b→3c→3d. Phenstatin (3b) was found to be a potent inhibitor of tubulin polymerization and the binding of colchicine to tubulin comparable to combretastatin A-4 (1b).

6 Claims, 5 Drawing Sheets

1a, R = OH, R₁ = OH
Combretastatin A-1
1b, R = OH, R₁ = H
Combretastatin A-4
1c, R = OSi(CH₃)₂C(CH₃)₃, R₁ = H
1d, R = OPO₃Na₂, R₁ = H
Combretastatin A-4 prodrug
1e, R = R₁ = H

2, Combretastatin A-2

3a, R = OSi(CH₃)₂C(CH₃)₃
3b, R = OH, Phenstatin
3c, R = OPO₃(C₆H₅CH₂)₂
3d, R = OPO₃Na₂
Phenstatin prodrug
3e, R = OCOCH₃
3f, R = H

4a, R = H, R₁,R₂ = OCH₂O
4b, R = R₂ = CH₃, R₁ = H
4c, R = H, R₁ = R₂ = OCH₃
4d, R = R₂ = OCH₃, R₁ = H
4e, R = R₂ = Cl, R₁ = H
4f, R = R₂ = F, R₁ = H

Scheme 1. Oxidation of Combretastatin A-4 silyl ether (1c) to phenstatin silyl ether (3a).

Figure 3.

Scheme 2

Figure 4.

Scheme 3

Figure 5.

SYNTHESIS OF PHENSTATIN AND PRODRUGS THEREOF

This application is a 371 U.S. National Stage of PCT/US99/00475 filed Jan. 9, 1999, and claims the benefit of U.S. provisional application 60/070,878 filed Jan. 9, 1998.

This research was funded in part by Outstanding Investigator Grant CA44344-01-09 awarded by the National Cancer Institute, DHHS. The United States government may have certain rights to this invention.

The present invention relates generally to compounds for use in the treatment of one or more neoplastic diseases and more particularly to the synthesis of the antineoplastic compound herein denominated "phenstatin" and water soluble prodrugs thereof.

By way of background, the elucidation and isolation of combretastatin A-4 is described in U.S. Pat. No. 4,996,237 which issued to G. R. Pettit et al., on Feb. 26, 1991, while early efforts to develop a combretastatin A-4 prodrug are described in U.S. Pat. No. 5,561,122, which issued to G. R. Pettit on Oct. 1, 1996. The general background information from each of those patents is incorporated herein by this reference thereto.

The potent cancer cell growth and tubulin assembly inhibitor combretastatin A-4 was originally isolated from the African tree *Combretum caffrum* (Combretaceae) circa 1985 and has been undergoing clinical development. The present disclosure comprises a benchmark in the continuing effort to synthesize practical water soluble prodrugs related to combretastatin A-4 and is a significant and remarkably unexpected extension of those early efforts which are described in U.S. Pat. No. 5,561,122, supra.

Figure 1:
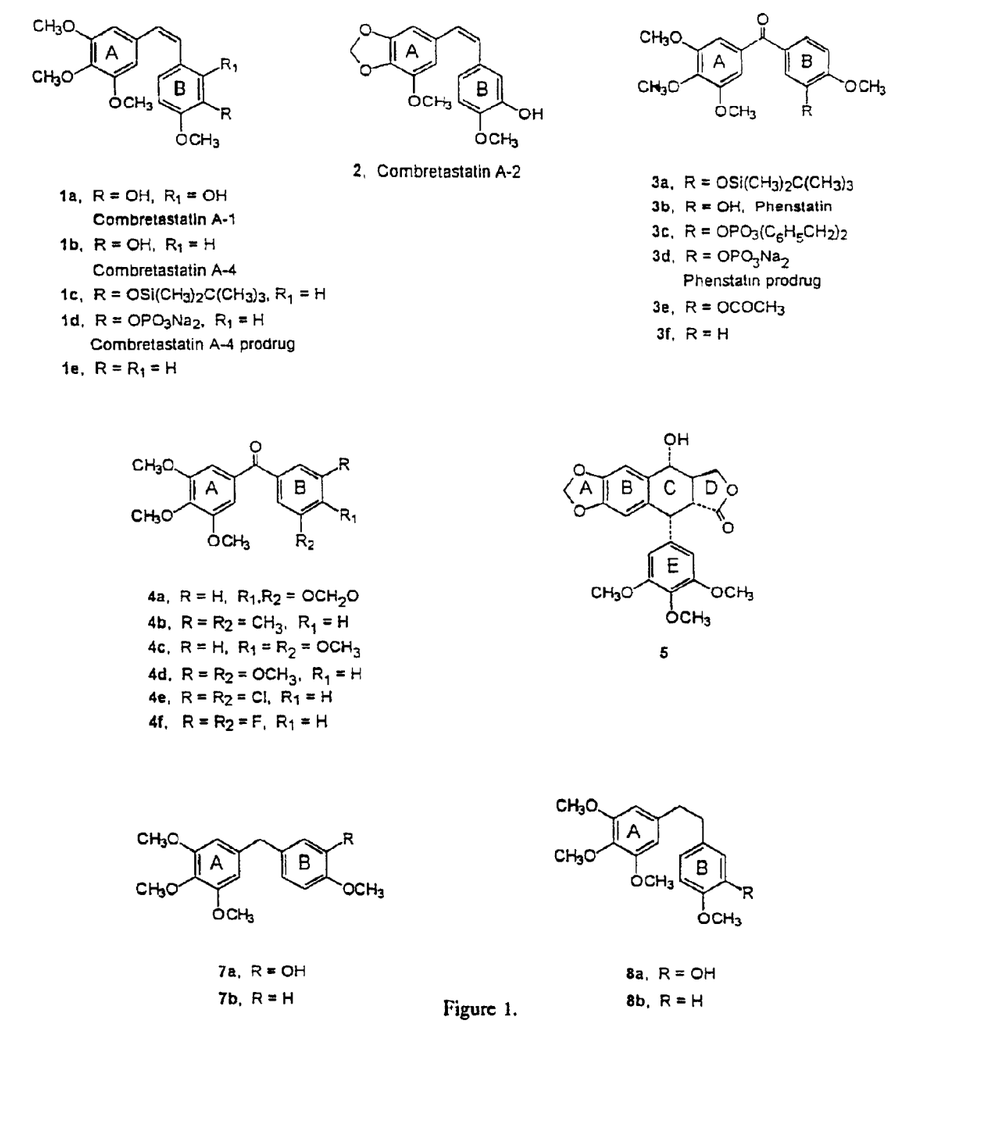
FIG. 1 is a display of the graphic structures of compounds 1–8 and selected derivatives thereof (as identified in the specification)

The African willow tree *Combretum caffrum* Kuntze (Combretaceae) has proven to be a very productive source of cancer cell growth (murine P388 lymphocytic leukemia) inhibitory stilbenes, bibenzyls and phenanthrenes (See: Pettit, et al., Antineoplastic Agents 291. Isolation and Synthesis of Combretastatins A-4, A-5, and A-6, *J. Med. Chem.* 1995, 38, 1666–1672). Since 1979 promising leads have been pursued which were focused on the three most active (inhibition of cancer cell growth and polymerization of tubulin (Id.)) constituents, namely combretastatin A-1 (1a), A-2 (2), and A-4 (1b)(Id.)(See, FIG. 1). Of these, combretastatin A-4 (1b) has reached clinical development as the very soluble prodrug 1d. Meanwhile other research groups have also been further extending structure/activity relationships (hereinafter referred to as "SAR") among the combretastatins (See: Bedford, et al., Synthesis of Water-Soluble Prodrugs of the Cytotoxic Agent Combretastatin A-4, *BioMed. Chem. Lett.* 1996, 6, 157–160) and related stilbenes (See: Kitanaka, et al., Oligomeric Stilbenes from *Caragana chamlagu* LAMARK Root, *Chem. Pharm. Bull* 1996, 44, 565–567).

Epoxidation of combretastatin A-4 silyl ether (1c)(Pettit et al., 1995, supra) using the Jacobsen chiral Mn (salen) complex (See: Popisil, et al., X-Ray Structural Studies of Highly Enantioselective Mn(salen) Epoxidation Catalysts, *Chem. Eur. J.* 1996, 2, 974–980) resulted in rearrangement and oxidation products (indicated by $^1$H-NMR and TLC analyses). Use of protecting groups is for the phenol offered no improvement and the absence of a protecting group resulted in apparent polymerization.

Figure 2:
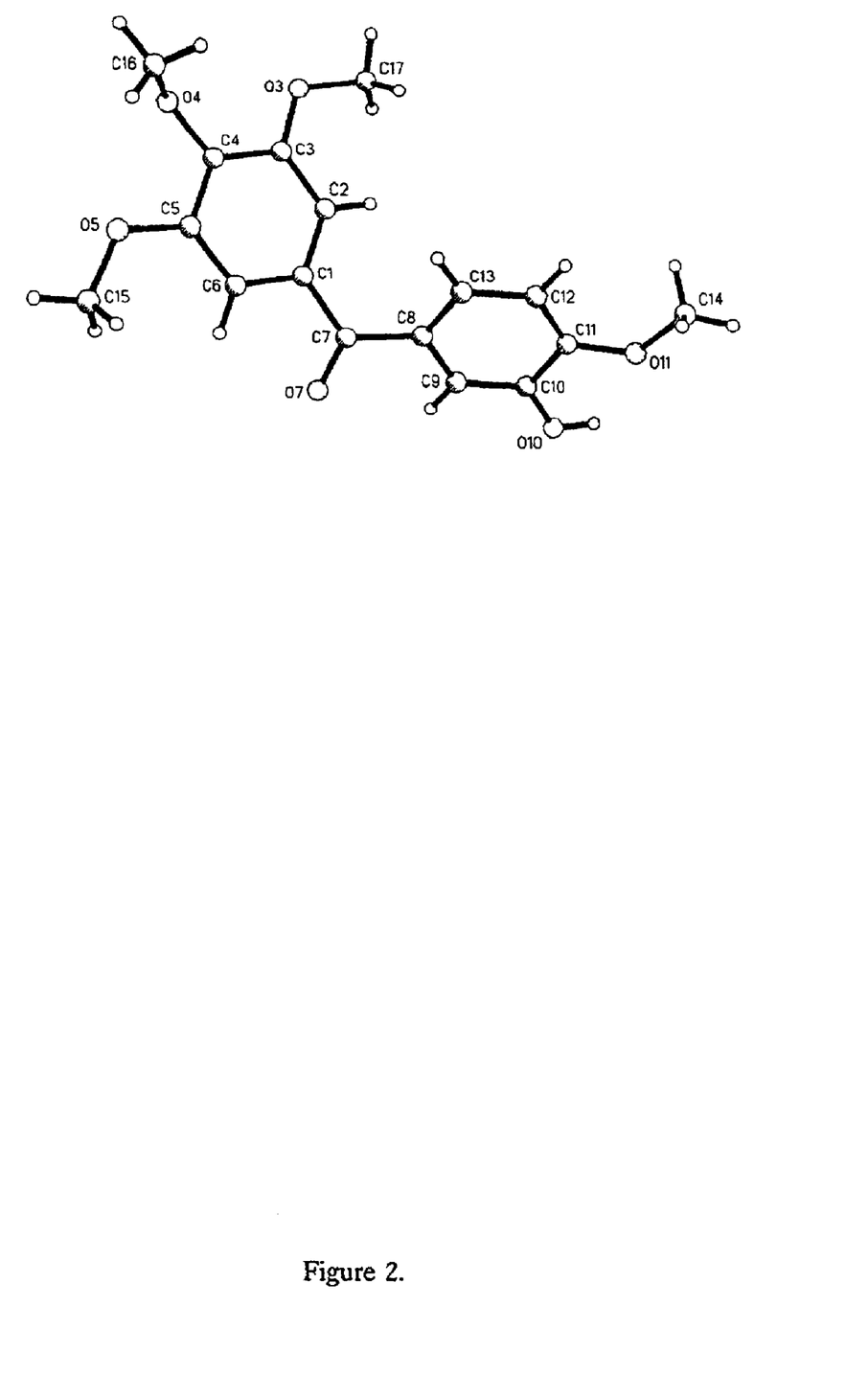
FIG. 2 is a computer generated perspective drawing of phenastatin (3b)
Figure 3:
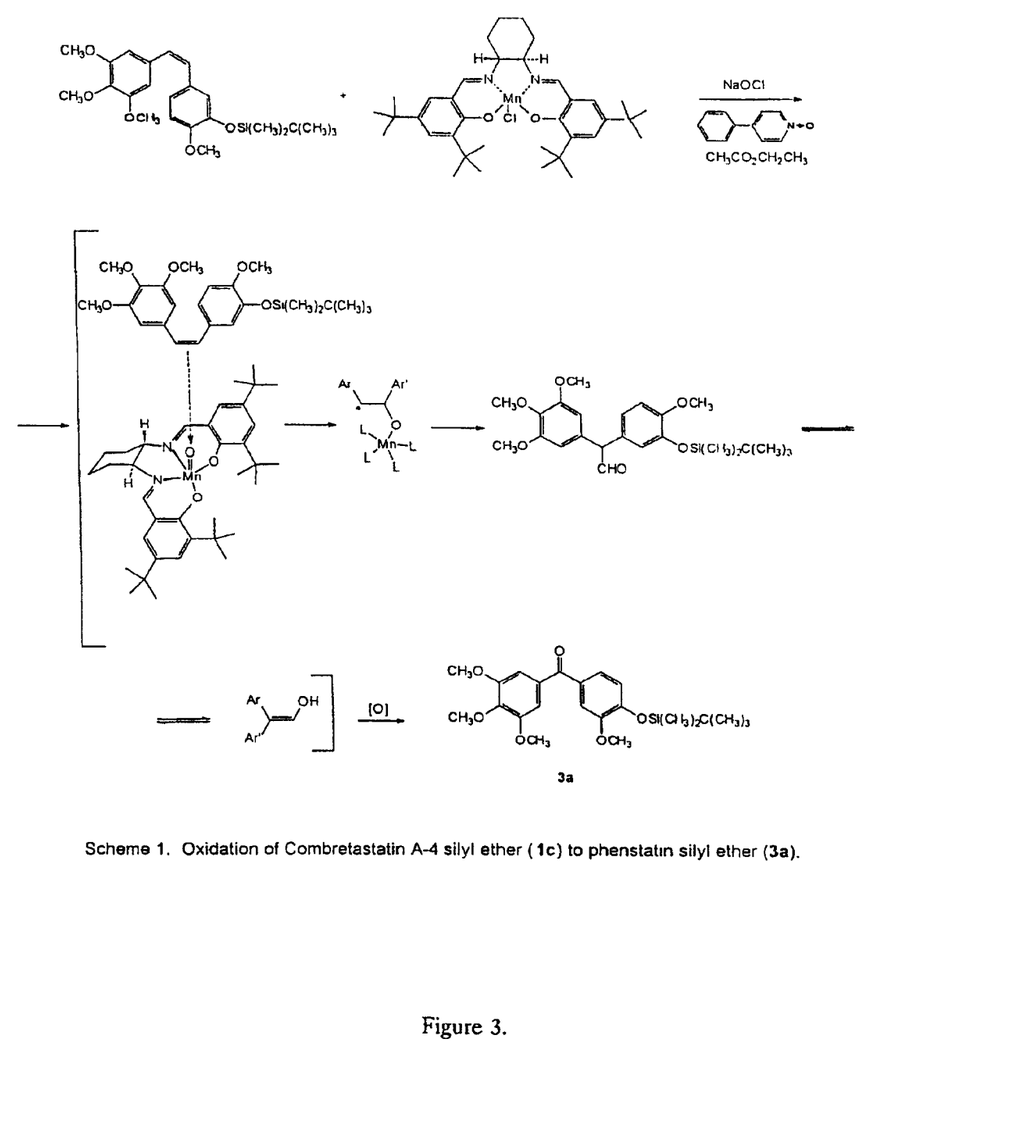
FIG. 3 is a flow diagram showing the oxidation of Combretastatin A-4 silyl ether (1c) to phenstatin silyl ether (3a)(herein "Scheme 1")

In the case of combretastatin A-4, the formation of the oxirane by the Jacobsen oxidation was observed by $^1$H-NMR, but the compound resisted isolation. In addition, the derived 1,1-diphenylacetaldehyde and benzophenone 3a products appeared to be formed. Following isolation of silyl ether 3a and mass spectral analysis of the suspected benzophenone (10% yield, 3b) cleavage of its silyl ether protective group showed the loss of one carbon atom. A conjugated carbonyl peak at 1633 cm$^{-1}$ was seen in the IR spectrum. Loss of the olefin bridge was established by NMR. This result suggested the need for structure confirmation of ketone 3b by X-ray crystallography, which demonstrated the compound was 3-hydroxy-3,4,4',5'-tetramethoxybenzophenone (FIG. 2). Finally, oxidative cleavage gave the silylated benzophenone 3a.

Because of the potent cancer cell line growth inhibition displayed by the deprotected benzophenone, it was denominated "phenstatin." The structure of phenstatin 3b proved to be closely related to the aromatic system of podophyllotoxin 5, a target of our efforts (Pettit, et al., Antineoplastic Agents V. The Aromatic System of Podophyllotoxin (Part B), *J. Med. Pharm. Chem.* 1962, 5, 800–808), which began in 1958, to locate the structural core responsible for the antineoplastic activity of this important lignan.

Figure 4:
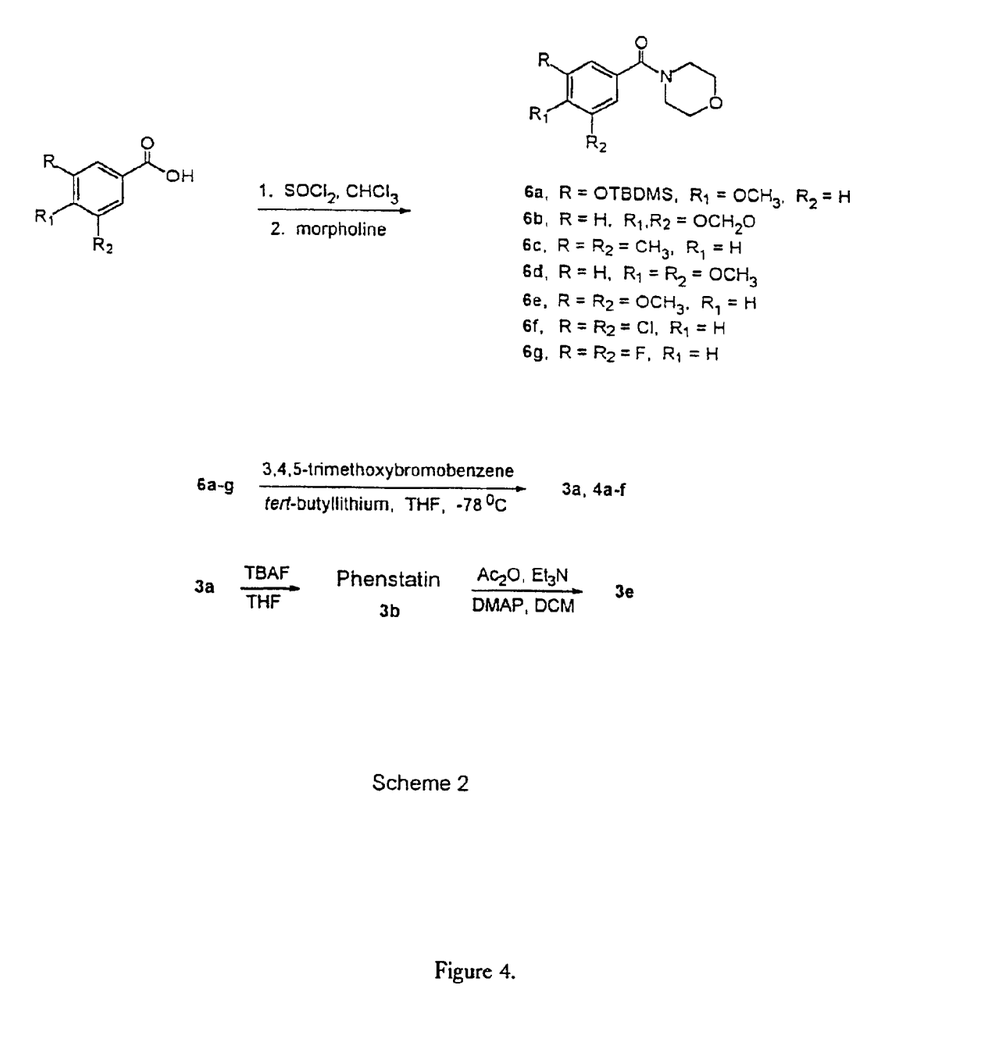
FIG. 4 is a flow diagram of the sequences herein referred to as "Scheme 2"

In order to improve the availability of phenstatin by a more efficient synthesis, several alternative routes were explored. The general procedure reported (Pettit et al., 1962, supra) in 1962 for obtaining ketone 4a based on a morpholine amide intermediate proved to be most effective. The phenstatin amide precursor was prepared from 3-(tert-butyldimethylsilyl)oxy-4-methoxybenzaldehyde by oxidation to the corresponding carboxylic acid using potassium permanganate, followed by conversion to the acid chloride, and finally treatment with morpholine (Scheme 2, FIG. 4). The amide 6a was allowed to react with the lithium derivative prepared from 3,4,5-trimethoxybromobenzene (See: Jung, et al., Stereoselective Synthesis of an Analogue of Podophyllotoxin by an Intramolecular Diels-Alder Reaction, *J. Org. Chem.* 1985, 50, 1087–1105) and t-butyllithium at −78° C. followed by deprotection to afford phenstatin 3b in 30% overall yield. Similarly, a series of related 4 benzophenones were synthesized for SAR purposes as shown in Table 1 below.

TABLE 1

Physical Properties of the Amides and Benzophenones.

| Compound | % Yield (from 5) | cryst. solvent | MP (° C.) | Formula (c)(d) |
|---|---|---|---|---|
| 6a | 94 | hexane | 66–67 | $C_{18}H_{29}NO_4Si$ |
| 6b | 88 | (a) | 87–88 | $C_{13}H_{17}NO_2$ |
| 6c | 73 | (a) | 78–79 | $C_{13}H_{17}NO_4$ |
| 6d | 78 | (a) | 84–85 | |
| 6e | 97 | (a) | 78–79 | $C_{13}H_{17}NO_4$ |
| 6f | 100 (g) | (a) | 117–119 | $C_{11}H_{11}Cl_2NO_2$ |
| 6g | 97 (g) | (b) | 68–70 | $C_{11}H_{11}F_2NO_2$ |
| 3a | 76 | hexane | 74–75 | $C_{23}H_{32}O_6Si$ |
| 3b | 83 | ethyl acetate-hexane | 149–150 | $C_{17}H_{18}O_6$ |
| 3c | 72 (e) | n/a | clear oil at r.t. | $C_{31}H_{31}O_9P$ |
| 3d | (f) | water-acetone | 165–167 | $C_{17}H_{17}O_9Na_2P$ |
| 3e | 93 (h) | ethyl acetate-hexane | 164–165 | $C_{19}H_{20}O_7$ |
| 4a | 98 | methanol | 124–125 | $C_{17}H_{16}O_6$ |
| 4b | 75 | hexane | 104–105 | $C_{18}H_{20}O_4$ |
| 4c | 53 | toluene-hexane | 120–122 | $C_{18}H_{20}O_6$ |
| 4d | 70 | hexane | 121–122 | $C_{18}H_{20}O_6$ |
| 4e | 34 | hexane | 131–132 | $C_{16}H_{14}Cl_2O_4$ |
| 4f | 36 | hexane | 121–123 | $C_{16}H_{14}F_2O_4$ |

Code:
(a) = crystallized following concentration of the flash column chromatography solvent.
(b) = crystallized at 0° C. upon isolation.
(c) = All compounds were subjected to combustion analysis for C and H (and for Cl, F, and N where appropriate). The results were within ±0.4% of the calculated values.
(d) = The $^1$H- and $^{13}$C-NMR data at 300 MHZ was also consistent with the assigned structure.
(e) = From 3b.
(f) = from 3c.

TABLE 1-continued

Physical Properties of the Amides and Benzophenones.

| Compound | % Yield (from 5) | cryst. solvent | MP (° C.) | Formula (c)(d) |
|---|---|---|---|---|

(g) = % Yield from acid chloride.
(h) = % yield from phenstatin.

Figure 5:
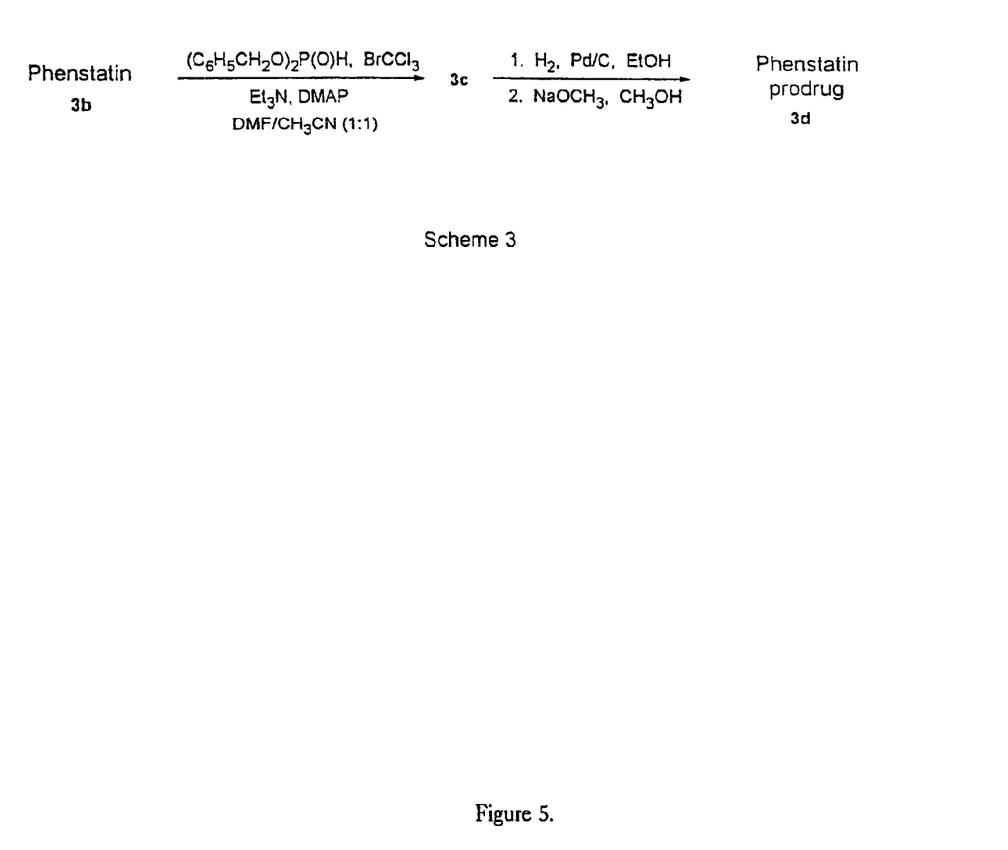
FIG. 5 is a flow diagram showing the conversion of phenstatin (3b) to phenstatin prodrug (3d)(as identified as "Scheme 3" in the specification).

Because of the improved therapeutic effects of the combretastatin A4 sodium phosphate 1d prodrug (Pettit, et al., Antineoplastic Agents 322. Synthesis of Combretastatin A-4 Prodrugs, *Anticancer Drug Design* 1995, 10, 299–309) when compared to the parent phenol 1b (Pettit, et al., Isolation and Structure of the Strong Cell Growth and Tubulin Inhibitor Combretastatin A4, *Experentia* 1989, 45, 209–211), the corresponding phenstatin prodrug 3d was synthesized (3b →3d, Scheme 3, FIG. 5). Both were used in the previous phosphorylation techniques (Pettit, et al., Antineoplastic Agents 322., *Anticancer Drug Design* 1995, supra; and Pettit, et al., Antineoplastic Agents 320. Synthesis of a Practical Pancratistatin Prodrug, *Anticancer Drug Design* 1995, 10, 243–250) for such syntheses, based on pentavalent and trivalent phosphorous precursors. However, they proved to be substantially less effective than the dibenzylphosphite approach (Silverberg, et al., A Simple, Rapid and Efficient Protocol for the Selective Phosphorylation of Phenols with Dibenzyl Phosphite, *Tetrahedron Lett.* 1996, 37, 771–774). The prodrug was synthesized in 3 steps from phenstatin via phosphorylation of phenol 3b employing dibenzylphosphite (under basic conditions in 1:1 acetonitrile—DMF)(Id), followed by cleavage of the benzyl groups 3c via catalytic hydrogenolysis (Pettit, et al., Antineoplastic Agents 320., *Anticancer Drug Design* 1995, supra) and reaction of the phosphoric acid product with sodium methoxide in methanol to afford sodium phosphate prodrug 3d in 56% overall yield.

Accordingly, the prime object of the present invention is to provide an economically viable method for the synthesis of phenstatin and prodrugs thereof which are water soluble and can be used in the preparation of useful antineoplastic preparations.

These and still further objects as shall hereinafter appear are readily fulfilled by the present invention in a remarkably unexpected manner as will be readily discerned from the following detailed description of an exemplary embodiment thereof especially when read in conjunction with the drawings attached hereto.

Compounds 3b, 3d, 1d, and 4a–f were comparatively evaluated in the NCI 60 cell-line human tumor screen (Boyd, Status of the NCI preclinical antitumor drug discovery screen. Implications for selection of new agents for clinical trial, CANCER: *Principles and Practices of Oncology Updates*, DeVita, et al. (Eds.), Lippincott: Philadelphia, 1989; Vol. 10, No. 3, pp. 1–12; Boyd, The Future of New Drug Development. Section I. Introduction to Cancer Therapy, *Current Therapy in Oncology*, Niederhuber, (Ed.), B. C. Decker, Inc.: Philadelphia, 1993; pp. 11–22; Boyd, et al., Data display and analysis strategies from NCI disease-oriented in vitro antitumor drug screen. In *Cytotoxic Anticancer Drugs: Models and Concepts for Drug Discovery and Development*, Valeriote, et al. (Eds.), Kluwer Academic Publishers: Amsterdam, 1992; pp. 11–34; Stinson, et al., Morphological and Immunocytochemical Characteristics of Human Tumor Cell Lines for Use in a Disease-Oriented Anticancer Drug Screen, *Anticancer Res.* 1992, 12,-1035–1054; Boyd, et al., Some Practical Considerations and Applications of the NCI in vitro Drug Discovery Screen, *Drug Dev. Res.* 1995, 34, 91–109). As illustrated in Table 2, below, the water soluble phenstatin phosphate prodrug 3d and the parent phenstatin 3b were essentially indistinguishable in potency (e.g., mean panel $GI_{50}$ values) and differential cytotoxicity profiles (e.g., Compare correlation coefficients). Moreover, 3d and 3b were quite similar to the combretastatin A-4 phosphate prodrug 1d both in terms of potency and differential cytotoxicity. In contrast, the related benzophenones 4a–f were generally much less potent than 3b, 3d or 1d, although their differential cytotoxicity profiles (and therefore their presumed mechanism of action (Boyd, et al., 1995, supra)) did not differ remarkably from the lead compound. Interestingly, the acetate derivative 3e of phenstatin exhibited significant human cancer cell line inhibitory activity: e.g., CNS U251 $GI_{50}$ 0.0039 μg/ml, pharynx FADU $G_{50}$ 0.0055 μg/ml and prostate DU-145 $GI_{50}$ 0.0029 μg/ml.

TABLE 2

Comparative Evaluations of Phenstatin 3b, Phenstatin Prodrug 3d, Combretastatin A-4 Prodrug 1d and Other Related Benzophenones 4a–f in the NCI 60 Cell-Line Human Tumor Screen[a]

| Compound | Mean Panel $GI_{50}$ (±S.D)[b] ... [×$10^{-8}$ M] | COMPARE Correlation Coefficient[b] |
|---|---|---|
| 3b | 6.01 (3.76) | 1.00 |
| 3d | 7.33 (4.54) | 0.94 |
| 1d | 1.28 (0.44) | 0.81 |
| 4a | 270. (21.4) | 0.74 |
| 4b | 348. (45.4) | 0.79 |
| 4c | 511. (52.5) | 0.74 |
| 4d | 54.3 (4.94) | 0.80 |
| 4e | 512. (69.8) | 0.73 |
| 4f | 494. (99.0) | 0.75 |

[a]Compounds were tested in triplicate in the NCI screen as described (Boyd, 1993, supra; Boyd, et al., 1995, supra; Weinstein, et al., An Information-Intensive Approach to the Molecular Pharmacology of Cancer, *Science* 1997, 275,-343–349) in each of three concentration ranges (HITEST (Boyd, et al., 1995, supra) $10^{-5}$, $10^{-6}$, and $10^{-7}$ M) using five, 10-fold dilutions within each range.
[b]Descriptions and methods of calculation are described elsewhere (Id.). COMPARE analyses were performed using the mean graph profiles (Id.) of phenstatin 3b as the seed.

Because of the known potent interactions of combretastatin A-4 1b (Pettit, et al., Antineoplastic Agents 291., *J. Med. Chem.* 1995, supra) and ketone 3f (Cushman, et al., Synthesis and Evaluation of Analogues of (Z)-1-(4-Methoxyphenyl)-2-(3,4,5-trimethoxyphenyl)ethene as Potential Cytotoxic and Antimitotic Agents, *J. Med. Chem.* 1992, 35, 2293–2306) with the colchicine site of tubulin and because of COMPARE studies, such as those shown in Table 2, which suggested similar mechanisms of action, phenstatin 3b, its prodrug 3d, and compounds 4a–4f were evaluated with others for potential inhibitory effects on tubulin polymerization and on the binding of colchicine to tubulin (Table 4, below).

In addition, comparative Murine P388 Lymphocytic Leukemia Cell Line and Human Cancer cell growth inhibitor for phenstatin 3b vs the phenstatin prodrug 3d and the combretastatin A4 prodrug 1d were conducted and are reported in Table 3, below.

TABLE 3

Comparative Murine P388 Lymphocytic Leukemia Cell Line and Human Cancer Cell Growth Inhibition for Phenstatin 3b vs. the Phenstatin Prodrug 3d and the Combretastatin A-4 Prodrug 1d.

| Cell Type | Cell Line $GI_{50}$ μg/ml | Phenstatin 3b | Phenstatin Prodrug 3d $GI_{50}$ μg/ml | Combretastatin A-4 Prodrug 1d |
|---|---|---|---|---|
| Leukemia | P388 | 0.0033 | <0.001 | 0.0004 |
| Ovarian | OVCAR-3 | 0.0023 | 0.0025 | 0.023 |
| CNS | SF-295 | 0.052 | 0.012 | 0.036 |
| Renal | A498 | 0.38 | 0.05 | 0.041 |
| Lung-NSC | NCI-H460 | 0.0057 | 0.035 | 0.029 |
| Colon | KM20L2 | 0.04 | 0.27 | 0.34 |
| Melanoma | SK-MEL-5 | 0.0038 | 0.0047 | 0.041 |

Simultaneous studies were performed for comparison of the new compounds with combretastatin A-4 1b, its prodrug 1d, and the related compounds 3f (Cushman, et al., 1992, supra), 1e (Cushman, et al., Synthesis and Evaluation of Stilbene and Dihydrostilbene Derivatives as Potential Anticancer Agents That Inhibit Tubulin Polymerization, *J. Med. Chem.* 1991, 34, 2579–2588), 7a (Getahun, et al., Synthesis of Alkoxy-Substituted Diaryl Compounds and Correlation of Ring Separation with Inhibition of Tubulin Polymerization: Differential Enhancement of Inhibitory Effects under Suboptimal Polymerization Reaction Conditions, *J. Med. Chem.* 1992, 35, 1058–1067), 7b (Cushman, et al., 1992, supra), 8a (Getahun, et al., 1992, supra), and 8b (Cushman, et al., 1991, supra).

TABLE 4

Inhibition of tubulin polymerization and colchicine binding by phenstatin, combretastatin A-4, and related compounds.[a]

| Compound | Inhibition of tubulin polymerization $IC_{50}$, μM ± $SD^b$ | Inhibition of colchicine binding % inhibition |
|---|---|---|
| 1b | 1.2 ± 0.1 | 97 |
| 1d | >80 | 4 |
| 1e | 1.3 ± 0.2 | 97 |
| 3b | 1.0 ± 0.2 | 86 |
| 3d | 21 ± 3 | 37 |
| 3e | 3.5 ± 0.5 | 71 |
| 4a | 15 ± 2 | 0 |
| 4b | 11 ± 2 | 7 |
| 4c | 15 ± 2 | 1 |
| 4d | 3.6 ± 0.8 | 58 |
| 4f | 39 ± 7 | 0 |
| 7a | 3.3 ± 0.5 | 65 |
| 7b | 4.4 ± 0.2 | 56 |
| 8a | 2.1 ± 0.3 | 77 |
| 8b | 3.2 ± 0.3 | 54 |

[a]Reaction conditions described in detail in the Experimental Section.
[b]SD, standard deviation.

Consistent with the relative antiproliferative activities summarized in Table 4, phenstatin 3b was equivalent to combretastatin A-4 1b in its interactions with tubulin in the assays used here. Confirming unpublished observations with other bulky substituents on the B ring hydroxyl, the combretastatin A4 prodrug 1d was totally inactive against purified tubulin, but, unexpectedly, the phenstatin prodrug 3d had weak activity in inhibiting assembly and moderate activity as an inhibitor of colchicine binding. In the latter assay the prodrug was about 40% as active as phenstatin.

Previous structure-activity studies (Cushman, et al., *J. Med. Chem.* 1992, supra; Getahun, et al., *J. Med. Chem.* 1992, supra; Cushman, et al., *J. Med. Chem.* 1991, supra) had demonstrated maximal activity with tubulin with a 2-carbon bridge in the Z-stilbene configuration, whether or not the B ring hydroxyl was present, and the data of Table 4 reiterate this conclusion. The tetramethoxy ketone 3f has shown increased activity relative to the analogous diphenylmethane 7b (Cushman, et al., *J. Med. Chem.* 1992, supra), but the recovery of activity versus the Z-stilbene 1e was incomplete. In contrast, in the presence of the B ring hydroxyl, the reduced activity of the diphenylmethane 7a was completely recovered in the ketone phenstatin 3b.

In terms of the effect of the B ring hydroxyl on interactions with tubulin, no significant difference was observed between the Z-stilbenes 1b and 1e, slight differences between the diphenylmethanes 7a and 7b and the dibenzyls 8a and 8b, and a small difference between the ketones 3b and 3f. When a difference was observed, it was always the phenol that had the greater activity.

Manipulation of molecular models demonstrated that it was possible to closely superimpose the two phenyl rings in the ketones with those in the Z-stilbenes, but this was also possible with the bibenzyls. This may indicate that tubulin specifically recognizes the $sp^2$ hybridization introduced with the carbonyl and stilbene bridges or the ring conjugation, analogous to that in colchicine, that these two bridges permit. The greater activity of 3b relative to 3f may also indicate that the B ring phenol group imposes steric constraints on the relative positions of the two phenyl rings.

The series of substituent modifications represented by compounds 4a–4f failed to yield a derivative superior to 3b as an inhibitor of either cell growth or tubulin polymerization. Compound 4a, which is closely analogous to the A, B, and E rings of podophyllotoxin 5, had only weak activity against tubulin, and this was comparable to that obtained with 4c. Compound 4c has vicinal methoxy groups, with the hydroxyl group of 3b replaced by a methoxyl group, instead of the methylenedioxy bridge of 4a. The best activity in this group of compounds was observed with di-meta methoxy groups in ring B 4d, but this compound was 3–4fold less potent than phenstatin in inhibiting tubulin polymerization. There was a further 3-fold drop in activity with di-meta methyl groups in ring B 4b, and compounds with halogens at these positions 4e and 4f were almost inert with tubulin. In the presence of a para methoxy group, the bulkiness of the substituent and/or the presence of an oxygen in the meta position of ring B seems to be critical for optimum inhibitory activity against tubulin in the ketone derivatives. A hydrogen 3f leads to greater inhibition than a methoxy or phosphate group 4c, 3d but is less effective than a hydroxyl 3b.

Based on the ring substituent structural modifications of phenstatin described herein, both the $sp^2$ hybridization of the carbonyl carbon that preserves the relative cis-relationship of the aromatic rings and the specific 3-hydroxy-4-methoxy-substitution appear necessary for strong cancer cell growth inhibition. Further development of phenstatin and its prodrug are in progress.

General Experimental Procedures. Ether (anhydrous diethyl ether), tetrahydrofuran (distilled from sodium and benzophenone), thionyl chloride and morpholine were distilled prior to use. Reagents were obtained from Sigma-Aldrich Co. Solvent extracts of aqueous solutions were dried over anhydrous magnesium sulfate unless otherwise noted. Flash column chromatography was performed using silica gel (230–400 mesh) and hexane-ethyl acetate as eluant.

ANALTECH silica gel GHLF plates were used for TLC. All compounds were visible with fluorescent short-wave light (254 nm).

Melting points were recorded employing an ELECTROTHERMAL 9100 apparatus and were uncorrected. $^1$H and $^{13}$C NMR spectra were recorded by means of a VARIAN VXR-300 instrument and referenced to chloroform. $^{31}$P-NMR was obtained from a VARIAN VXR-500 and referenced to an external standard (85% aqueous $H_3PO_4$). Mass spectral data were recorded using a VARIAN MAT 312 instrument (EIMS), and IR spectra were determined with a MATTONSON INSTRUMENTS 2020 GALAXY SERIES FTIR instrument. X-ray crystal structure data collection was performed on an ENRAF-NONIUS CAD4 diffractometer.

Jacobsen Oxidation of Combretastatin A-4 1b

To a mixture of 4-phenylpyridine-N-oxide (0.127 g, 0.74 mmol) and (R,R)-(-)-[N,N$^1$-bis(3,5-di-tert-butylsalicylidene)-1.2-cyclohexanediaminoat(2-)] manganese(III) chloride (Palucki, et al., Highly Enantioselective, Low-Temperature Epoxidation of Styrene, J. Am. Chem. Soc. 1994, 116, 9333–9334) (0.024 g, 0.037 mmol) in a 50 mL flask was added a solution of 3'[(tert-butyldimethylsilyl)oxy]combretastatin A-4(1c, 0.80 g, 1.86 mmol) in 3 Ml of ethyl-acetate (or methylene chloride). The mixture was stirred at 4° C. for 20 minutes followed by addition of an aqueous 0.50 M NaOCl solution (6.32 mL, 3.16 mmol) via syringe. The temperature remained at 4° C., and reaction progress was monitored by TLC (4:1 hexane-EtOAc). After 5 h, the reaction mixture was warmed to room temperature, and the aqueous phase removed. The organic layer was washed successively with water (2×10 mL) and brine (10 mL) and dried over anhydrous $Na_2SO_4$. Filtration and solvent removal in vacuo gave a brown residue that was subjected to flash column chromatography (4:1 hexane-ethyl acetate, 1"×12" column). The silyl ether protected benzophenone 3a (Rf=0.27) was collected as a yellow oil. A second flash column chromatographic separation was necessary for final purification. Consistent 10% yields were obtained based on conversion of combretastatin A-4 silyl ether to phenstatin (3b, see below).

Phenstatin 3b.

Silyl ether 3a (4.90 g, 11.3 mmol) was dissolved in dry tetrahydrofuran (100 mL), and 1.0 M tetrabutylammonium fluoride (11.3 mL, 11.3 mmol) was added (slowly via syringe) while rapidly stirring under Ar (Pietikäinen, Tetrahedron Lett. 1995, supra). After 15 min, ice (20 g) and ether (100 mL) were added successively. The ethereal layer was washed with water (3×100 mL), dried, filtered, and solvent removed under reduced pressure to yield a yellow solid. Flash chromatography (eluant:3:2 hexane-ethyl acetate, Rf=0.17) was performed and afforded an off-white solid that recrystallized from hexane as colorless granules: EIMS m/z (peak height) 318 (M$^+$, 100%), 303 (14%), 195 (30%), 151 (36%). IR (Nujol, cm$^{-1}$) 1633 (C=O), 1604 (aromatic C=C); $^1$H-NMR (CDCl$_3$) δH 7.406 (1H, dd, J$_{6/2}$ 2.1 Hz, J$_{6/2}$ 9.4 Hz, H-6), 7.362 (1H, d, J$_{2/6}$ 2.1 Hz, H-2), 7.011 (2H, s, H-2', 6'), 6.906 (1H, d, J$_{5/6}$ 8.4 Hz, H-5), 5.662 (1H, s, —OH), 3.969 (3H, s, 4'-OCH$_3$), 3.913 (3H, s, 4-OCH$_3$), 3.860 (6H, s, 3', 5'-OCH$_3$); $^{13}$C-NMR (75.5 MHZ, CDCl$_3$, assignments deduced with assistance from an APT spectrum) δC 193.3 (C=O), 152.8 (C-3', 5'), 150.2 (C4), 145.3 (C-3), 141.7 (C-4'), 133.2 (C-1'), 131.1 (C-1), 123.6 (C-6), 116.2 (C-2), 110.0 (C-5), 107.5 (C-2', 6'), 60.9 (4-OCH$_3$), 56.3 (3', 5'-OCH$_3$), 56.1 (4'-OCH$_3$).

Phenstatin Acetate 3e.

Acetic anhydride (74 μL, 0.79 mmol) was added to a solution of phenstatin (3b, 0.2 g, 0.63 mmol), DMAP (7.8 mg, 0.063 mmol) and triethylamine (0.13 mL, 0.94 mmol) in dry methylene chloride (1.5 mL, under argon at room temperature). The yellow solution was stirred for 30 min (reaction was complete by TLC). Methanol (5 Ml) was added and the reaction mixture concentrated to a solid that was washed with diethyl ether (3 ×10 mL) and partitioned between ethyl acetate and cold Ln hydrochloric acid. The organic layer was washed with 10% aqueous sodium bicarbonate and dried. Solvent removed, in vacuo, gave an off-white solid that was recrystallized from ethyl acetate-hexane to give colorless snowflakes of analytical purity: EIMS m/z (peak height) 360 M$^+$, 60%), 318 (100%), 303 (10%), 195 (20%), 151 (30%), 91 (32%), 44 (25%). $^1$H-NMR (CDCl$_3$)δ H 7.740 (1H, dd, J$_{6/2}$ 2.1 Hz, J$_{6/5}$ 8.1 Hz, H-6). 7.556 (1H, d, J$_{2/6}$ 2.1 Hz, H-2), 7.026 (1H, d, J$_{5/6}$ 8.0 Hz, H-5), 7.013 (2H, s, H-2', 6'), 3.914 (3H, s, 4-OCH$_3$), 3.907 (3H, s, 4'-OCH$_3$), 3.863 (6H, s, 3', 5'-OCH$_3$), 2.315 (3H, s, —OCOCH$_3$).

X-Ray Crystal Structure Determination of Phenstatin 3b.

Colorless crystals of ketone 3b were grown as clusters of thick plates from an ether solution. Cleavage of a single crystal fragment from one of the clusters provided a usable specimen (0.54×0.32×0.28 mm), which was mounted on the end of a glass capillary tube. Data collection was performed at 25±1° C. Crystal data: $C_{17}H_{18}O_6$, monoclinic space group P2$_1$/c with a=12.608(2), b=14.858(2), c=8.738(3)Å, β=104.69(2)°, V=1583.3(12)Å$^3$, λ(CuKα)=1.54178 Å, $\rho_0$=1.299 g cm$^{-3}$, $\rho_c$=1.335 g cm$^{-3}$ for Z=4 and F.W. =318.31, F(000)=672. The structure determined for 3b converged to the standard crystallographic residual of R$_1$=0.0462 for 2453 reflections in which Fo>4.0 sigma(Fo) and 0.0480 for all 2610 reflections. The corresponding wR2 Sheldrick values, based on Fo$^2$, were 0.1454 and 0.1475, respectively. The Goodness of Fit for all data was 1.042. Final bond distances and angles were all within acceptable limits.

3-(tert-butyldimethylsilyl)oxy-methoxybenzoic acid.

To a solution of 3-[tert-butyldimethylsilyl)oxy]-4-methoxy-benzaldehyde$^2$ (35.0 g, 131 mmol) in acetone (400 mL) was added (stirring) a warm solution (40° C.) of potassium permanganate (35.3 g, 223 mmol) in water (50 mL)-acetone (250 mL) over 30 min. The reaction mixture was stirred for 45 min (complete by TLC analysis). The suspension was cooled and filtered through a pad of celite, and the filtrate concentrated. The residue was dissolved in ethyl acetate (1000 mL) and transferred to a separatory funnel containing 1 N HCl (800 mL). The organic layer was extracted with water (5×1000 mL), brine (500 mL), dried (sodium sulfate), and solvent removed in vacuo to give a crystalline powder. Recrystallization from hexane afforded the benzoic acid as colorless needles (31.0 g, 84% yield): mp=163.5–164.5° C.; EIMS m/z (peak height) 282 (M$^+$), 267 (2%), 225 (92%), 210 (100%), 195 (20%).; IR (Nujol, cm$^{-1}$) 3100 (broad O—H stretch), 1682 (C=O), 1681 (aromatic C=C); $^1$H-NMR (CDCl$_3$) δH 7.732 (1H, dd, J$_{6/2}$ 2.2 Hz, J$_{6/5}$ 8.4 Hz, H-6), 7.569 (1H, d, J$_{2/6}$ 1.2 Hz, H-2), 6.894 (1H, d, J$_{5/6}$ 8.5 Hz, H-5), 3.882 (3H, s, —OCHR$_3$) 1.009 (9H, s, —Ot—Bu), 0.174 (6H, s, —Si(CH$_2$)$_2$); $^{13}$C-NMR (75.5 MHZ, CDCl$_3$, assignments assisted by an APT spectrum) δC 172.9 (C=O), 156.6 (C-4), 145.4 (C-3), 125.7 (C-2), 123.0 (C-6), 122.4 (C-1), 111.5 (C5), 55.8 (—OCH$_3$), 25.9 (—CH$_3$), —4.5 (—Si(CH$_2$)$_2$_), -4.5 (—Si—C—).

General Procedure for Synthesis of Morpholine Amides 6a–g.

To a 1.0 M solution of the carboxylic acid chloroform at room temperature was added 2 equivalents of thionyl chloride. The solution was heated to reflux under Ar until TLC (3:1 hexane-ethyl acetate) showed no starting material (approximately 4–8 h). The solution was concentrated to an oil that solidified under high vacuum (0.05 mm Hg), and the crude acid chloride was used in the next step without purification. Two equivalents of morpholine were slowly injected via syringe over a 5 min period to a 0.3 M solution of the acid chloride in toluene (under Ar). The reaction mixture was stirred at room temperature until the starting acid chloride was consumed (approx. 1.5–4 h, according to TLC using 3:1 hexane-ethyl acetate). The solution was filtered through a pad of celite to remove morpholine hydrochloride, and the pad washed with toluene. The filtrate was concentrated to an oil that was subjected to flash column chromatography. Concentration of the respective fractions led to the respective amides (Table 1). 6f and 6g were synthesized from the acid chloride.

N-[(3-tertbutyldimethylsilyl)oxy-4-methoxybenzoyl]morpholine 6a.

A cotton-like solid followed chromatography (eluant:hexane-ethyl acetate 3:2 1:4) and recrystallization from hexane (Table 1). EIMS m/z (peak height) 351 (M$^+$), 336 (4%), 294 (100%), 278 (26%), 265 (8%), 193 (70%), 165 (16%).

N-(3,5-dimethylbenzoyl)morpholine 6b.

After chromatography (3:2 hexane-ethyl acetate, Rf=0.19), a fluffy-appearing solid was obtained (Table 1).

N-(3,4-dimethoxybenzoyl)morpholine 6c.

Amide 6c was obtained as a colorless flaky solid (Gardner, et al., The Polyoxyphenols of Western Red Cedar (Thuja Plicata Donn), *Can. J. Chem.* 1960, 38, 2387–2394) following chromatography (1:2 hexane-ethyl acetate, Rf=0.16).

N-(3,4-methylenedioxybenzoyl)morpholine 6d.

Amide 6d (Kasztreiner, et al., Synthesis and Pharmacological Investigation of New Alkoxybenzamides II, *Biochem. Pharmacol.* 1962, 11, 651–657) was isolated as a colorless flaky solid following chromatography (1:1 hexane-ethyl acetate, Rf=0.22).

N-(3,5-dimethoxybenzoyl)morpholine 6e.

After chromatographic (1:1 hexane-ethyl acetate Rf=0.18) purification amide 6e was collected as a colorless solid. TOF mz/251.6 (M$^+$).

N-(3,5-dichlorobenzoyl)morpholine 6f.

The clear oily product crystallized at 0°C.: EIMS m/z (peak height) 259 (M$^+$), 261 (M+2), 263 (M+4), 258 (M$^+$-H), 175 (62%), 173 (96%), 86 (76%), 56 (100%).

N-(3,5-difluorobenzoyl)morpholine 6g.

Amide 6g (Rf=0.21 in 3:2 hexane-ethyl acetate) gave EIMS m/z (peak height) 227 (M$^+$), 141 (100%), 113 (50%), 86 (36%), 56 (66%).

General Procedures for Synthesis of Benzophenones 3a, 4a–f A flame-dried flask containing a 0.1 M solution of 3,4,5-trimethoxybromobenzene (1.1 eq in dry tetrahydrofuran) was cooled to −78° C., evacuated to 1 Torr and refilled with Ar for 10 cycles. To this solution was slowly added tert-butyllithium (2.2 eq), and the reaction mixture was stirred for 15 min. A second dry flask containing a 0.1 M solution of the morpholine amide (1.0 eq) in tetrahydrofuran was cooled to −78° C., evacuated, and refilled with Ar. The phenyllithium reagent was transferred via cannula to the amide solution. The reaction mixture was stirred at −65 to −78° C. for 4 h, followed by a slow warming to room temperature. Progress of the reaction was monitored by TLC (hexane-ethyl acetate). The reaction was stopped by adding 6 eq of isopropyl alcohol and stirring for 1 h. Water was added, and the mixture was extracted with ether (3×). The ethereal extracts were combined, washed with water, dried, and solvent removed to give an oil that was subjected to flash chromatography. Collection and concentration of the required fractions afforded the benzophenone (Table 1).

3-(tert-butyldimethylsilyl)oxy-3',4,4',5'-tetramethoxybenzophenone 3a.

Using amide 6a (0.2 g, 0.57 mmol), 3,4,5-trimethoxybromobenzene (0.169 g, 0.683 mmol), and t-BuLi (0.74 mL, 1.25 mmol) the above scheme led to crude phenstatin silyl ether 3a (0.199 g, Rf=0.29 in 4:1 hexane-ethyl acetate). Purification and recrystallization from hexane afforded large glass-like prisms (Table 1); EIMS m/z (peak height) 432 (M$^+$), 417 (2%), 402 (1%), 375 (100%), 360 (58%), 345 (4%), 193 (26%).

3,4,5-trimethoxy-3',4'-methylenedioxybenzophenone 4a.

Flash column chromatography (4:1 hexane-ethyl acetate Rf=0.20) and recrystallization from methanol afforded small colorless needles (Pettit, et al., *J. Med. Pharm. Chem.* 1962, supra).

3,4,5-trimethoxy-3',5'-dimethylbenzophenone 4b.

Chromatography (9:1 hexane-ethyl acetate Rf=0.19) and recrystallization from hexane yielded off-white needles: EIMS m/z (peak height) 300 (M$^+$, 100%), 285 (14%), 270 (4%), 375 (100), 195 (40%).

3,3',4,4',5-pentamethoxybenzophenone 4c.

Purification by column chromatography (4:1 hexane-ethyl acetate Rf=0.10) and recrystallization from toluene-hexane gave an off-white powder: EIMS m/z (peak height) 332 (M$^+$, 100%), 317 (6%), 301 (8%), 195 (16%), 165 (22%).

3,3',4,5,5'-pentamethoxybenzophenone 4d.

After recrystallization from hexane, the off-white powder did not require chromatographic purification: EIMS m/z (peak height) 332 (M$^+$, 100%), 317 (6%), 301 (8%), 195 (16%), 165 (22%).

3,5-dichloro-3',4',5'-trimethoxybenzophenone 4e.

Chromatographic (9:1 hexane-ethyl acetate, Rf=0.28) separation and recrystallization from hexane afforded clear diamond-shaped crystals: EIMS m/z (peak height) 340 (M$^+$, 100%), 342 (M+2), 344 (M+4), 325 (26%), 310 (4%) 195 (46%).

3,5-difluoro-3',4',5'-trimethoxybenzophenone 4f.

Following chromatography (9:1 hexane-ethyl acetate, Rf=0.21) and recrystallization from hexane, the ketone was obtained as colorless needles: EIMS m/z (peak height) 318 (M$^+$, 100%), 293 (20%), 278 (4%), 195 (22%), 141 (36%), 113 (16%).

3-O-Dibenzylphosphoryl-phenstatin 3c.

To a dry flask equipped with septum, magnetic stirrer, thermometer and Ar inlet containing dry acetonitrile (50 mL) and DMF (50 mL) was added phenstatin (3b, 2.0 g, 6.28 mmol). Upon cooling to −10° C., bromotrichloromethane (3.10 mL, 31.4 mmol) was added followed by triethylamine (1.84 mL, 13.2 mmol) and dimethylaminopyridine (77 mg, 0.63 mmol). After one minute, dropwise addition of dibenzylphosphite was begun while maintaining a temperature of −7 to −10° C. The resultant yellow solution was monitored by TLC (1:1 hexane-ethyl acetate, Rf=0.19) until complete. At that time (1.5 h), 0.5 M aqueous KH$_2$PO$_4$ (50 mL) was added followed by extraction with ethyl acetate (3×100 mL). The organic extract was washed successively with water (200 mL), brine (150 mL), and dried (sodium sulfate). The solution was filtered and concentrated m vacuo to a milky oil. Flash column chromatography (eluant: 1:1 hexane-ethyl acetate) was performed to give benzyl phosphate 3c as a clear oil (2.60 g, 72% yield): EIMS m/z (peak height)(578, M$^+$), (486, 4%), (91, 100%). $^1$H-NMR (CDCl$_3$) δH 7.694 (1H, d, J$_{6/5}$ 8.0 Hz, H-6), 7.657 (1H, s, H-2), 7.319 (10H, s, Ar—H), 7.025 (2H, s, H-2',6'), 7.000 (1H, d, J$_{5/6}$ 9.0 Hz, H-5), 5.182 (4H, d, J 8.5 Hz-O—CH$_2$—Ph), 3.88 (9H, s, 3', 5', 4-OCH$_3$); $^{31}$P-NMR (CDCl$_3$, decoupled, 202.35 MHZ) δP -5.22.

Disodium Phenstatin 3-O-phosphate 3d.

The benzyl phosphate (3c, 0.68 g, 1.18 mmol) was added to anhydrous ethyl alcohol (denatured, 50 mL) in a dry flask equipped with a magnetic stirrer. After evacuating the vessel and refilling with Ar (two cycles), 5% palladium-on-carbon (0.58 g) was added. The flask was evacuated and refilled with H$_2$ to 10 psi (3×). The mixture was stirred vigorously for 15 min and filtered through a 1 cm pad of celite. The flask and celite were washed with ethanol and solvent was removed under reduced pressure to afford a foamy tan solid (0.44 g) that was used in the next step.

The deprotected phosphate (0.44 g, 1.10 mmol) was dissolved in anhydrous methanol (15 mL) and sodium methoxide (88 mg, 2.20 mmol) was added at room temperature. The cloudy solution was stirred for 20 hours and the reaction mixture was concentrated to a white solid that was washed with 2-propanol and recrystallized (3×) from water-acetone. The phenstatin prodrug (3d, 0.38g, 78% yield) was collected by filtration and found to give; LRFAB m/z 443.02 (M+H+), calculated 443.048, EIMS m/z (peak height) 318 (100%, M+—PO$_3$Na$_2$+H), 303 (12%), 195 (20%), 151 (23%); $^1$H-NMR (D$_2$O) δH 7.644 (1H, t, J$_{2/6}$1.8 Hz, H-2), 7.366 (1H, dd, J$_{6/2}$ 1.8 Hz, J$_{6/5}$8.5 Hz, H-6), 7.006 (1H, d, J$_{5/6}$ 8.5 Hz, H-5), 6.933 (2H, s, H-2', 6'), 3.844 (3H, s, 4'-OCH$_3$), 3.748 (6H, s, 3', 5'-OCH$_3$) 3.734 (3H, s, 4OCH$_3$); $^{13}$C-NMR (D$_2$O, reference to CDCl$_3$) δC 193.5 (C=O), 151.1; and $^{31}$P-NMR (D$_2$O, decoupled, -202.35 MHZ) δP -1.965. The solubility of phenstatin prodrug 3d was found to be 30 mg/mL in distilled water at 25° C.

Tubulin Assays.

Electrophoretically homogeneous bovine brain tubulin was purified from bovine brain as described previously (Hamel, et al., Separation of active tubulin and microtubule-associated proteins by ultracentrifugation and isolation of a component causing the formation of microtubule bundles, *Biochemistry* 1984, 23, 4173–4184). Reaction mixtures (0.24 mL during preincubation, 0.25 mL during incubation, with all concentrations referring to the final volume) contained 0.8 M monosodium glutamate (taken from 2.0 M stock solution adjusted to pH 6.6 with Hcl), 1.0 mg/mL (10 μM) tubulin, 4% (v/v) dimethyl sulfoxide, and varying concentrations of drug. Samples were incubated for 15 min at 30° C. and chilled on ice. GTP, required for polymerization, was added in 10 μL to a final concentration of 0.4 mM. Samples were transferred to cuvettes held at 0° C. by electronic temperature controllers in GILFORD model 250 recording spectrophotometers. Baselines were established, and the reaction was initiated by a jump (approximately 1 min) to 30° C. Extent of assembly after 20 min was the parameter used to determine IC$_{50}$ values. Active compounds were examined in at least three independent experiments, and inactive compounds were generally evaluated twice. In most experiments, four spectrophotometers were used, with two control reaction mixtures.

The binding of [$^3$H]colchicine to tubulin was measured on DEAE-cellulose filters as described elsewhere (Kang, et al., N-acetylcolchinol O-methyl ether and thiocolchicine, potent analogs of colchicine modified in the C ring: Evaluation of the mechanistic basis for their enhanced biological properties, *J. Biol. Chm* 1990, 265, 10255–10259). Reaction mixtures contained 0.1 mg/mL (1.0 μM) tubulin, 5.0 μM [3H]colchicine, and 5.0 μM inhibitor and were incubated for 10 min at 37° C.

Dosing.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 20 mg/kg; intramuscular, 1 to about 50 mg/kg; orally, 5 to about 100 mg/kg; intranasal instillation, 5 to about 100mg/kg; and aerosol, 5 to about 100 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies either phenstatin 3b and/or phenstatin prodrug 3d, and/or benzophenones 4a–f or any other compound described herein.

Composition "A"

Hard-gelatin Capsules

One thousand two-piece hard gelatin capsules for oral use, each capsule containing 200 mg of an active ingredient are prepared from the following types and amounts of ingredients:

| Active ingredient, micronized | 200 g |
|---|---|
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

Composition "C"

Tablets

One thousand tablets, each containing 200 mg of an active ingredient, are prepared from the following types and amounts of ingredients:

| Active ingredient, micronized | 200 g |
|---|---|
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, is prepared from the following types and amounts of ingredients:

| | |
|---|---|
| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

Composition "E"

Parenteral Product

A sterile aqueous suspension for parenteral injection, containing 30 mg of an active ingredient in each milliliter for treating a neoplastic disease, is prepared from the following types and amounts of ingredients:

| | |
|---|---|
| Active ingredient, micronized | 30 g |
| POLYSORBATE 80 | 5 g |
| Methylparaben | 2.5 g |
| Propylparaben | 0.17 g |
| Water for injection, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

Composition "F"

Suppository, Rectal and Vaginal

One thousand suppositories, each weighing 2.5 g and containing 200 mg of an active ingredient are prepared from the following types and amounts of ingredients:

| | |
|---|---|
| Active ingredient, micronized | 15 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

Composition "G"

Intranasal Suspension

One liter of a sterile aqueous suspension for intranasal instillation, containing 20 mg of an active ingredient in each milliliter, is prepared from the following types and amounts of ingredients:

| | |
|---|---|
| Active ingredient, micronized | 15 g |
| POLYSORBATE 80 | 5 g |
| Methylparaben | 2.5 g |
| Propylparaben | 0.17 g |
| Deionized water, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

Composition "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

Composition "J"

Insufflation

One hundred grams of an active ingredient in bulk form is finely divided by means of an air micronizer.

The foregoing composition is useful for treating a neoplastic disease, by the inhalation of 300 mg one to four times a day.

From the foregoing, it becomes readily apparent that a new and useful antineoplastic factor and new and useful antineoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention.

What is claimed is:

1. A method of synthesizing phenstatin comprising the steps of:

oxidizing 3-(tert-butyl dimethylsilyl)oxy-4-methoxybenzaldehyde with potassium permanganate to form the corresponding carboxylic acid;

converting said carboxylic acid to the corresponding acid chloride;

treating said acid chloride with the lithium derivative obtained from 3,4,5-trimethoxybenzene and t-butyllithium to form a protected product; and deprotecting said protected product to form phenstatin.

2. A method of synthesizing phenstatin prodrug comprising the steps of:

phosphorylating phenstatin with dibenzylphosphite in the presence of bromodichloromethane to form a phosphate ester;

cleaving the benzyl groups from said phosphate ester by means of catalytic hydrogenolysis; and reacting the cleaved phosphate ester with sodium methoxide to produce the phenstatin sodium phosphate prodrug.

3. A method of inhibiting cancer cell growth and tubulin polymerization in an environment inflicted therewith comprising: introducing into said environment a pharmaceutically acceptable carrier and a small but effective amount of phenstatin prodrug.

4. Phenstatin prodrugs and derivatives thereof having the structure:

wherein when R=H and $R_1$=$OCH_3$, $R_2$ is $OPO_3Na_2$ or $OCOCH_3$ and when R=$R_2$, $R_2$ is $OCH_3$, $CH_3$, Cl or F and $R_1$ is H.

5. A method of inhibiting human cancer cell growth in a host inflicted therewith comprising administering to said host in a pharmaceutically acceptable carrier a small but effective amount of a compound selected from the group consisting of phenstatin, phenstatin prodrug and the derivatives thereof having the structure wherein when R=H and $R_1$=$OCH_3$, $R_2$ is $OPO_3Na_2$, $OCOCH_3$ or $OCH_3$ and when R=$R_2$, $R_2$ is $OCH_3$, $CH_3$, Cl or F and $R_1$ is H and when $R_1$=$R_2$, $R_2$ is $OCH_3$ and R is H.

6. A method of inhibiting human cancer cell growth in a host inflicted therewith comprising administering to said host in a pharmaceutically acceptable carrier a small but effective amount of a compound selected from the group consisting of phenstatin, phenstatin prodrug and the derivatives thereof having the structure wherein when $R_1$=$R_2$, $R_2$ is $OCH_2O$ and R is H.

* * * * *

UNITED STATES PATENT AND TRADEMARK OFFICE
CERTIFICATE OF CORRECTION

| | | |
|---|---|---|
| PATENT NO. | : 6,943,194 B1 | Page 1 of 1 |
| APPLICATION NO. | : 09/582952 | |
| DATED | : September 13, 2005 | |
| INVENTOR(S) | : Pettit et al. | |

It is certified that error appears in the above-identified patent and that said Letters Patent is hereby corrected as shown below:

Column 1, lines 9 and 10, "may have" should be changed to --has--.

Signed and Sealed this

Twenty-eighth Day of April, 2009

JOHN DOLL
*Acting Director of the United States Patent and Trademark Office*